United States Patent [19]

Burckhalter

[11] Patent Number: 4,762,117

[45] Date of Patent: Aug. 9, 1988

[54] METHOD OF SURGICAL INTERVENTION FOR REMOVAL OF FLUORESCABLE GLASS FRAGMENTS

[76] Inventor: Joseph H. Burckhalter, 203 Commodore Club, 995 N. A1A Hwy., Indialantic, Fla. 32903

[21] Appl. No.: 21,461

[22] Filed: Mar. 4, 1987

Related U.S. Application Data

[63] Continuation-in-part of Ser. No. 699,244, Feb. 5, 1985, abandoned.

[51] Int. Cl.$^4$ ............................................... A61B 1/05
[52] U.S. Cl. ................................... 128/1 R; 128/737; 128/665
[58] Field of Search ............... 128/1 R, 737, 654, 664, 128/665; 252/301.4 F, 301.6 P

[56] References Cited

U.S. PATENT DOCUMENTS

| | | | |
|---|---|---|---|
| 3,459,673 | 8/1969 | Best et al. | 252/301.4 F |
| 3,522,190 | 7/1970 | Turner et al. | 252/301.4 F |
| 3,634,711 | 1/1972 | Barber et al. | 252/301.4 FX |
| 3,867,303 | 2/1975 | Shaw et al. | 252/301.6 P |
| 3,869,403 | 3/1975 | Shaw et al. | 252/301.18 |
| 3,869,405 | 3/1975 | Shaw et al. | 252/301.65 |
| 4,184,196 | 1/1980 | Monet et al. | 128/665 X |
| 4,195,329 | 3/1980 | Woog | 128/665 X |
| 4,675,529 | 6/1987 | Kushida | 128/665 X |

OTHER PUBLICATIONS

Kinsey et al., "Endoscopic System . . . Detection of Fluorescence" Rev. Sci. Instrum. 51(10) Oct. 1980, pp. 1403–1406.

*Primary Examiner*—Edward M. Coven
*Attorney, Agent, or Firm*—Krass and Young

[57] ABSTRACT

A method of visualizing fragments of glass fragments at a trauma site is provided, for use in a case associated with traumatic injury due to fragmentation of a glass object and implantation at the trauma site. The glass is of a type which under darkfield ultraviolet excitation has the property of emitting visualizable fluorescence and is thus adapted for surgical intervention for purposes including assessment of the extent of implantation, control of infection, and removal of fragments from the site of trauma.

4 Claims, No Drawings

METHOD OF SURGICAL INTERVENTION FOR REMOVAL OF FLUORESCABLE GLASS FRAGMENTS

CROSS-REFERENCE TO A RELATED APPLICATION

This application is a continuation-in-part of copending application Ser. No. 699,244, filed Feb. 5, 1985, abandoned.

TECHNICAL FIELD

The present invention pertains to fragmentable or fracturable glass objects, panel structures and the like that in whole form or fragmented form fluoresce, and use thererof. In a method aspect, such an object or structure, when factured and fragmented in an event associated with traumatic injury, permits surgical intervention and visualization of the trauma site for the professional assessment of the presence, location or absence of the fluorescing foreign body fragments, and for removal of the fragments.

BACKGROUND OF THE INVENTION

Traumatic injury in an event associated with fracture and fragmentation of conventional glass objects and structures (e.g., glass wool, fiberglass, automobile windshields, eye glass lenses, picture windows, window walls, sky lights, etc.) has often presented a difficult medical problem for the attending surgeon. The problem is difficult with respect to examination of the trauma site (visual or by X-ray, e.g.) for the presence or absence of implanted foreign body fragments. Location and surgical removal of the fragments are usually even more difficult. In a typical case, the examination, location and complete removal of implanted fragments can require a long course of treatments lasting for months in a clinical or hospital setting. In such a case, the fragments are of various sizes and shapes and have sharp edges. The fragments can over time migrate in a given organ or tissue so that early surgical removal is a first priority for wound healing and rehabilitation.

It is therefore an object of the present invention to provide means for visualizing fragments, especiallty inconspicuous or implanted fragments of glass objects fractured in an event associated with traumatic injury.

It is a further object to provide means for visualizing a surgical examination field for the presence or absence of implanted glass fragments at a trauma site, especially sites of facial injury or head injury.

These and other objects, features and advantages of the invention will become apparent from the following description.

SUMMARY AND DETAILED EXAMINATION

In one preferred embodiment, the invention concerns a method of visualizing fragments of glass at a trauma site resulting from the fracture of a glass object. The glass object which may be conventional is of the type that is fracturable into glass fragments that in an event associated with traumatic injury can become traumatically implanted. The glass is of the type that is light transmissive and fluoresces in a dark field under excitation by means of ultraviolet light, the invention being based on the discovery that not only does the glass fluoresce in a dark field so that it can be visualized but also the fragments themselves of widely varying sizes and shapes strongly emit visualizable fluorescence even when implanted in tissue at a trauma site. Examples of glass objects contemplated include household articles such as kitchen glassware, glass wool, fiberglass, monofilaments and filament fragments, fiberglass wool, motor vehicle or automobile windshields, eyeglass lenses, laboratory glassware. ornamental glass objects, glass containers, picture windows, window walls, ski lights, components of any of the above, etc. For purposes of description herein, the glass fragments occurring at a trauma site are classified in three categories: large fragments (greater than 0.5 mm. in the maximum viewable dimension) that are conspicuous in a lightfield, i.e., ordinary light; small fragments (less than 0.5 mm in the maximum viewable dimension) that are inconspicuous in a lightfield; and large and/or small fully implanted fragments, the fragments of the first two categories, sometimes referred to herein as surface fragments, occurring at the surface of the traumatized tissue and, if implanted, only partly so much that the fragments can receive excitation by ultraviolet light directly without attentuation due to blockage by tissue. In a preferred form, the intensity of exposure or excitation employed for visualization of the glass is selected for maximal excitation such that the dimensionally smallest implanted fragments can be visualized. Visualization is accomplished by means of darkfield-fluorescence as indicated, preferably with the aid of magnification with a device such as a magnifying glass or spectacle lens which visualization means may be per se conventional. A suitable UV-lamp for the purpose is the shortwave ultraviolet lamp, series UV5-54, commercially available from Ultra-Violet Products, Inc. The UV-lamp may be hand-held or stationary. The visualization means may include photomultiplier means. It is found surprisingly that UV-excitation of a trauma site in a darkfield serves to visualize readily substantially all the surface fragments (both large and small, as defined) and some if not most of the implanted fragments (both large and small). By contrast, in a lightfield (i.e., using visible light only) especially where the fragments are colorless glass fragments, only surface fragments are visible. For example, in a case which is typical, fragments of a fluorescable opthalmic lens (having the composition of lime glass, code 8361) containing titanium dioxide as a fluorescent minor component (cf. *Glass Engineering Handbook*, 3rd ed., 1984, page I-10, McGraw-Hill, New York, incorporated herewith by reference) were implanted in a trauma site simulating a human cutaneous tissue model (porcine rind, rectilinear, ca. 6×11 cm.). The fragments in situ were of various shapes and sizes classified (estimated) as follows:

| Maximum Fragment (mm.) Dimension | | Fluorescent Distribution, % of Total | | |
|---|---|---|---|---|
| | | Surface | Implanted Partial | Complete |
| Large: | more than 0.5 to ca.4 | 10% | 10% | 10% |
| Small: | less than 0.5 | 20% | 20% | Balance |

It is further estimated in this illustrative case that, by the present method in its first phase, about 70% of the fluorescence can be readily removed surgically by grasping the thus visualized fragments one by one using appropriate tools such as tweezers or forceps and removing the fluorescence without causing further undue trauma. This initial removal procedure has several advantages according to the invention. It is efficient, prompt, and reduces the major bulk of the foreign particle burden from the wound site. This latter burden includes all the surface fragments and some of the implanted fragments. It also importantly exposed sub-surficial fluorescence which might otherwise go undetected. In a further phase which can be an extension of the first phase or can be a latter operation, the thus exposed fluorescence can also be removed. It is an unexpected feature of the invention that a significant fluorescence is due to totally implanted fragments, i.e., fragments below the surface of the tissue. The invention contemplates that fragments remaining after the first phase can in large part by effectively removed by probing until all or substantially all the fragments are visualized.

The glass objects that fracture into fragments that are detectable by the method of the invention typically are fabricated from an optical quality host glass having a fluorescent color additive or component in an amount sufficient to enable the fragments to fluoresce in a darkfield under UV light. A preferred component for purposes of fluorescence according to the invention is a metal oxide such as titanium dioxide ($TiO_2$). The content of $TiO_2$ is preferably in the range from about 0.5% to about 1.5% of the host glass. In one preferred case this additive is one that contributes rare earth ions to the glass. Exemplary additives are neodymium compounds (U.S. Pat. Nos. 3,867,303, 3,869,403 and 3,869,405; Scientific Encyclopedia, pages 1183–1186, 5th Ed., Van-Nostrand, New York, 1976) and oxides of samarium, europium, terbium, dysporsium, and thulium (Baran et al., J. Dent. Res. 56, 1323, 1977). Host glasses containing the additives emit variously colored fluorescence under excitation at a wavelength, for example, of about 360 nanometers. The observed colors are red-orange (Sm), pink (Eu), yellow-green (Tb), yellow (Dy), purple (Tm), and orange (Dy and Sm). The glass making materials are of high purity and free of contamination from iron or other elements which if present in the glass would cause light absorption at the primary fluorescence wavelength. Examples of glasses which exhibit fluorescence at a wavelength of 1.06 micrometers are the following:

A borate glass consisting of about 98 weight percent of a host glass consisting of 20 and 80 mol percent of $B_2O_3$ and 20 to 80 mol percent of a glass modifier selected from $Bi_2O_3$ and a combination of ZnO and $P_2O_5$, and approximately 2 weight percent $Nd_2O_3$ contributing trivalent neodymium to the glass.

An acetate glass consisting of about 6 weight percent of $Nd(C_2H_3O_2)_3$ in a host glass selected from $Pb(C_2H_3O_2)_2$, $KC_2H_3O_2$, $NaC_2H_3O_2$, $Ca(C_2H_3O_2)_2$ and combinations thereof, the $Nd(C_2H_3O_2)_3$ contributing trivalent neodymium ions to the glass.

A sulfate glass consisting of 98 weight percent of a host glass which consists essentially of 90 mol percent of the glass former $AnCl_2$ and 10 mol percent of the glass modifier $Na_2SO_4$ and 2 weight percent of $Nd_2(SO_4)_3$.

A fluoroborate glass consisting of about 98 weight percent of a host glass consisting essentially of 10 to 50 mol percent of $B_2O_3$, 25 to 45 mol percent of $AlF_3$ and 25 to 45 mol percent of $PbF_2$ and approximately 2 weight percent of $NdF_3$.

For surgical intervention in visualizing fragments of glass at a trauma site resulting from fracture of a glass object that is fluorescable under ultraviolet light, as described, the method of the invention includes exposing the trauma site to darkfield ultraviolet light of intensity such that conspicuous fragments are caused to fluoresce and their presence and location to be thus visualized and confirmed whereby the visualization is likewise sufficient and is thereby confirmed to be sufficient to advantageously reveal the presence and location of the small fragments and implanted fragments, viewing the darkfield for the presence and location of fluorescent sites, and surgically removing the sites from the darkfield.

Thus while the invention, the best mode of practicing the same, and preferred embodiments are described in detail in the foregoing specification, it will be realized by those skilled in the art that considerable variation can be made in such detail without departing from the spirit and scope of the claims which follow.

I claim:

1. For surgical intervention, a method of visualizing and removing fragments of glass at a trauma site resulting from fracture of a glass object that is fluorescable under ultraviolet light, the fragments typically being of various sizes and shapes including surface fragments comprising (1) large fragments that are conspicuous both in a lightfield and a darkfield, and (2) small fragments that are conspicuous in a darkfield and inconspicuous in a lightfield, and sub-surface fragments comprising (3) large and/or small implanted fragments that are inconspicuous in a lightfield, the method comprising:

exposing the trauma site to darkfield ultraviolet light of intensity such that said conspicuous surface fragments are caused to fluoresce and their presence and location to be thus visualized and confirmed whereby the visualization is likewise sufficient after removal of said surface fragments in a first phase to advantageously reveal the presence and location of said sub-surface implanted fragments in a further phase, viewing the darkfield for the presence and location of fluorescent sites, and surgically removing the sites from the darkfield in said first phase and said further phase thereby reducing the major bulk of the glass particle burden from the trauma site.

2. A method of visualizing implanted glass fragments according to claim 1 where the fluorescable property of the glass object is due to the presence of titanium dioxide.

3. A method of visualizing implanted glass fragments according to claim 1 or claim 2 including the step of probing to enable better visualization of submerged fluorescent sites.

4. A method according to claim 1 or claim 2 where the removal step is extended until the darkfield is free of fluorescence.

* * * * *